(12) United States Patent
Brown et al.

(10) Patent No.: US 6,423,879 B1
(45) Date of Patent: Jul. 23, 2002

(54) SELECTIVE PARA-XYLENE PRODUCTION BY TOLUENE METHYLATION

(75) Inventors: Stephen H. Brown, Princeton, NJ (US); Mark F. Mathias, Pittsford, NY (US); Robert A. Ware, Wyndmoor, PA (US); David H. Olson, Pennington, NJ (US)

(73) Assignee: ExxonMobil Oil Corporation, Fairfax, VA (US)

( * ) Notice: Subject to any disclaimer, the term of this patent is extended or adjusted under 35 U.S.C. 154(b) by 0 days.

(21) Appl. No.: 09/341,008

(22) PCT Filed: Oct. 2, 1997

(86) PCT No.: PCT/US97/18079

§ 371 (c)(1),
(2), (4) Date: Nov. 15, 1999

(87) PCT Pub. No.: WO98/14415

PCT Pub. Date: Apr. 9, 1998

(51) Int. Cl.[7] .............................. C07C 1/20; C07C 2/66; B01J 19/06; B01J 29/00
(52) U.S. Cl. .......................... 585/467; 585/469; 502/60; 502/65; 502/71; 502/73; 502/77; 502/85; 502/245
(58) Field of Search ................................ 585/466, 467, 585/469; 502/60, 65, 71, 73, 77, 85, 214

(56) References Cited

U.S. PATENT DOCUMENTS

| 4,380,685 A | * | 4/1983 | Chu | 585/466 |
| 4,491,678 A | * | 1/1985 | Oda et al. | 585/466 |

* cited by examiner

*Primary Examiner*—Thuan D. Dang

(57) ABSTRACT

There is provided a process for the selective production of para-xylene which comprises reacting toluene with methanol in the presence of a catalyst comprising a porous crystalline material having a Diffusion Parameter for 2,2 dimethylbutane of about 0.1–15 sec$^{-1}$ when measured at a temperature of 120° C. and a 2,2 dimethylbutane pressure of 60 torr (8 kPa). The porous crystalline material is preferably a medium-pore zeolite, particularly ZSM-5, which has been severely steamed at a temperature of at least 950° C. The porous crystalline material is preferably combined with at least one oxide modifier, preferably including phosphorus, to control reduction of the micropore volume of the material during the steaming step.

10 Claims, 3 Drawing Sheets

SELECTIVE PARA-XYLENE PRODUCTION BY TOLUENE METHYLATION

Figure 1:
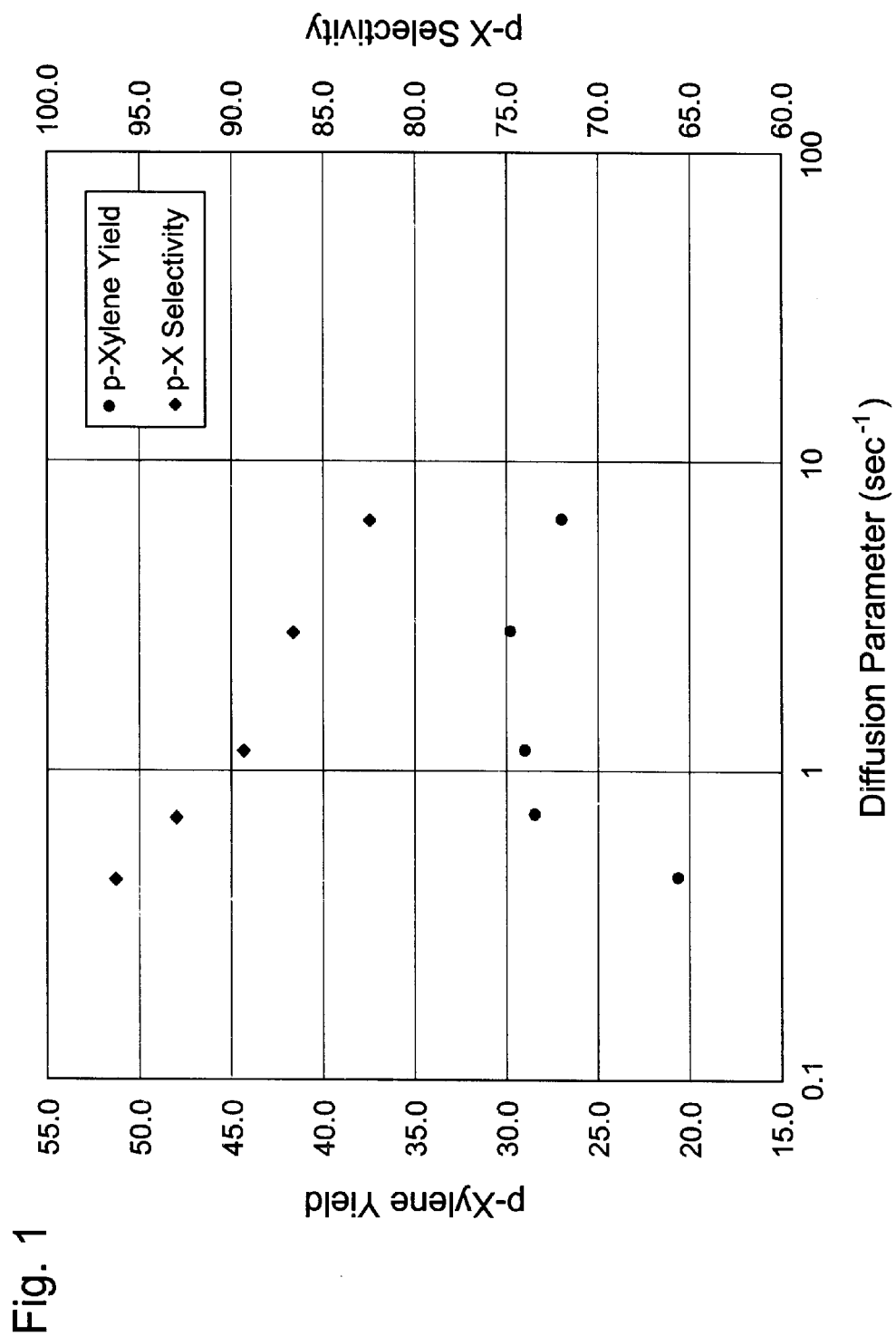

There is provided a process for the selective production of para-xylene by catalytic methylation of toluene in the presence of a solid catalyst. There is also provided a method for preparing a catalyst which is particularly suited for this reaction.

Of the xylene isomers, para-xylene is of particular value since it is useful in the manufacture of terephthalic acid which is an intermediate in the manufacture of synthetic fibers. Equilibrium mixtures of xylene isomers either alone or in further admixture with ethylbenzene generally contain only about 24 wt. % para-xylene and separation of p-xylene from such mixtures has typically required superfractionation and multistage refrigeration steps. Such processes have involved high operation costs and resulted in only limited yields. There is therefore a continuing need to provide processes which are highly selective for the production of p-xylene.

One known method for producing xylenes involves the alkylation of toluene with methanol over a solid acid catalyst. Thus the alkylation of toluene with methanol over cation-exchanged zeolite Y has been described by Yashima et al. in the Journal of Catalysis 16, 273–280 (1970). These workers reported selective production of para-xylene over the approximate temperature range of 200 to 275° C., with the maximum yield of para-xylene in the mixture of xylenes, i.e. about 50% of the xylene product mixture, being observed at 225° C. Higher temperatures were reported to result in an increase in the yield of meta-xylene and a decrease in production of para and ortho-xylenes.

U.S. Pat. No. 3,965,209 to Butter et al. and U.S. Pat. No. 4,067,920 to Kaeding teach processes for producing para-xylene in low conversion and high selectivity by reaction of toluene with methanol over a zeolite having a Constraint Index of 1–12, such as ZSM-5. In Butter et al the zeolite is steamed at a temperature of 250–1000° C. for 0.5–100 hours to reduce the acid activity of the zeolite, as measured by its alpha activity, to less than 500 and preferably from in excess of zero to less than 20.

U.S. Pat. No. 4,001,346 to Chu relates to a process for the selective production of para-xylene by methylation of toluene in the presence of a catalyst comprising a crystalline aluminosilicate zeolite which has undergone prior treatment to deposit a coating of between about 15 and about 75 wt. % of coke thereon.

U.S. Patent No. 4,097,543 to Haag et al. relates to a process for the selective production of para-xylene (up to about 77%) by disproportionation of toluene in the presence of a crystalline aluminosilicate catalyst which has undergone precoking to deposit a coating of at least about 2 wt. % coke thereon.

U.S. Pat. No. 4,380,685 to Chu relates to a process for para-selective aromatics alkylation, including the methylation of toluene, over a zeolite, such as ZSM-5, which has a constraint index of 1–12 and which has been combined with phosphorus and a metal selected from iron and cobalt. Chu indicates that the catalyst can optionally be modified (without specifying the effect of the modification) by steaming at a temperature of 250–1000° C., preferably 400–700° C. for 0.5–100 hours, preferably 1–24 hours.

U.S. Pat. No. 4,554,394 to Forbus and Kaeding teach the use of phosphorus-treated zeolite catalysts for enhancing para-selectivity in aromatics conversion processes. U.S. Pat. No. 4,623,633 to Young relates to the use of thermal shock calcination of aluminosilicates to produce up to 66% para-xylene selectivity.

The use of phosphorus modified ZSM-5 fluid bed catalysts as additive catalysts to improve the olefin yield in fluid catalytic cracking (FCC) is described in U.S. Pat. No. 5,389,232 to Adewuyi et al. and in U.S. Pat. No. 5,472,594 to Tsang et al.

According to the invention, it has now been found that certain porous crystalline materials having specific and closely defined diffusion characteristics, such as can be obtained by unusually severe steaming of ZSM-5 containing an oxide modifier, exhibit improved selectivity for the alkylation of toluene with methanol such that the xylene product contains at least about 90% of the paraisomer isomer at per-pass toluene conversions of at least about 15%.

In one aspect, the invention resides in a process for the selective production of para-xylene which comprises reacting toluene with methanol under alkylation conditions in the presence of a catalyst comprising a porous crystalline material having a Diffusion Parameter for 2,2-dimethylbutane of about 0.1–15 sec$^{-1}$ when measured at a temperature of 120° C. and a 2,2-dimethylbutane pressure of 60 torr (8 kPa).

Preferably, the porous crystalline material has a Diffusion Parameter of about 0.5–10 sec$^{-1}$.

Preferably, the catalyst contains at least one oxide modifier and more preferably at least one oxide modifier selected from oxides of elements of Groups IIA, IIIA, IIIB, IVA, VA, VB and VIA of the Periodic Table. Most preferably the oxide modifier is selected from oxides of boron, magnesium, calcium, lanthanum and most preferably phosphorus.

Preferably, the catalyst contains about 0.05 to about 20, more preferably about 0.1 to about 10 and most preferably about 0.1 to about 5, wt % of the oxide modifier based on elemental modifier.

Preferably, the catalyst has an alpha value less than 50 and preferably less than 10.

In a further aspect, the invention resides in a method for producing a catalyst for use in the selective production of para-xylene by reacting toluene with methanol, said method comprising the steps of:
(a) starting with a porous crystalline material having a Diffusion Parameter for 2,2-dimethylbutane in excess of 15 sec$^{-1}$ when measured at a temperature of 120° C. and a 2,2-dimethylbutane pressure of 60 torr (8 kPa); and
(b) contacting the material of step (a) with steam at a temperature of at least about 950° C. to reduce the Diffusion Parameter thereof for 2,2-dimethylbutane to about 0.1–15 sec$^{-1}$ when measured at a temperature of 120° C. and a 2,2-dimethylbutane pressure of 60 torr (8 kPa), the micropore volume of the steamed material being at least 50% of the unsteamed material.

Preferably, said porous crystalline material used in step (a) comprises an aluminosilicate zeolite having a silica to alumina molar ratio of at least 250.

The present invention provides a process for alkylating toluene with methanol to selectively produce p-xylene in high yield and with a high per-pass conversion of toluene. The process employs a catalyst which comprises a porous crystalline material having a Diffusion Parameter for 2,2-dimethylbutane of about 0.1–15 sec$^{-1}$, and preferably 0.5–10 sec$^{-1}$, when measured at a temperature of 120° C. and a 2,2-dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q\infty$, where $Q\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material employed in the process of the invention is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1–12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. No. 5,304,698 to Husain; U.S. Pat. No. 5,250,277 to Kresge et al.; U.S. Pat. No. 5,095,167 to Christensen; and U.S. Pat. No. 5,043,503 to Del Rossi et al., the disclosure of which patents are incorporated by reference.

Preferably, the zeolite employed in the process of the invention is ZSM-5 having a silica to alumina molar ratio of at least 250, as measured prior to any treatment of the zeolite to adjust its diffusivity.

The medium pore zeolites described above are preferred for the process of the invention since the size and shape of their pores favor the production of p-xylene over the other xylene isomers. However, conventional forms of these zeolites have Diffusion Parameter values in excess of the 0.1–15 $sec^{-1}$ range required for the process of the invention. The required diffusivity for the present catalyst can be achieved by severely steaming the catalyst so as to effect a controlled reduction in the micropore volume of the catalyst to not less than 50%, and preferably 50–90%, of that of the unsteamed catalyst. Reduction in micropore volume is derived by measuring the n-hexane adsorption capacity of the catalyst, before and after steaming, at 90° C. and 75 torr n-hexane pressure.

Steaming of the porous crystalline material is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Most preferably, said at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt. %, and preferably is between about 0.1 and about 10 wt. %, based on the weight of the final catalyst.

Where the modifier includes phosphorus, incorporation of modifier in the catalyst of the invention is conveniently achieved by the methods described in U.S. Pat. Nos. 4,356.338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3–5 hours.

Similar techniques known in the art can be used to incorporate other modifying oxides into the catalyst of the invention.

Representative phosphorus-containing compounds which may be used to incorporate a phosphorus oxide modifier into the catalyst of the invention include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, (RO)P (OX)$_2$, secondary, (RO)$_2$POX, and tertiary, (RO)$_3$P, phosphites, and esters thereof such as the monopropyl ester, alkyl dialkylphosphinites, (RO)PR$_2$, and dialkyl alkyphosphinite, (RO)$_2$PR, esters. Corresponding sulfur derivatives may also be employed including (RS)$_2$P(S)H, (RS)$_2$P(S)R, (RS)P(S)R$_2$, R$_2$PSX, (RS)P(SX)$_2$, (RS)$_2$PSX, (RS)$_3$P, (RS)PR$_2$, and (RS)$_2$PR. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, (RO)PCl$_2$, dialkylphosphorochloridites, (RO)$_2$PCl, dialkylphosphinochloroidites, R$_2$PCl, alkyl alkylphosphonochloridates. (RO)(R)P(O)Cl, dialkyl phosphinochloridates, R$_2$P(O)Cl, and RP(O)Cl$_2$. Applicable corresponding sulfur derivatives include (RS)PCl$_2$, (RS)$_2$PCl. (RS)(R)P(S)Cl, and R$_2$P(S)Cl.

Particular phosphorus-containing compounds include ammonium phosphate, ammonium dihydrogen phosphate, diammonium hydrogen phosphate, diphenyl phosphine chloride, trimethylphosphite. phosphorus trichloride, phosphoric acid, phenyl phosphine oxychloride, trimethylphosphate, diphenyl phosphinous acid, diphenyl phosphinic acid, diethyichlorothiophosphate, methyl acid phosphate, and other alcohol-P$_2$O$_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylae, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmoillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composed with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20–200 microns.

The catalyst of the invention may optionally be precoked. The precoking step is preferably carried out by initially utilizing the uncoked catalyst in the toluene methylation reaction, during which coke is deposited on the catalyst surface and thereafter controlled within a desired range, typically from about 1 to about 20 wt. % and preferably from about 1 to about 5 wt. %, by penodic regeneration by exposure to an oxygen-containing atmosphere at an elevated temperature.

One of the advantages of the catalyst described herein is its ease of regenerability. Thus, after the catalyst accumulates coke as it catalyzes the toluene methylation reaction, it can easily be regenerated by burning off a controlled amount of coke in a partial combustion atmosphere in a regenerator at temperatures in the range of from about 400 to about 700° C. The coke loading on the catalyst may thereby be reduced or substantially eliminated in the regenerator. If it is desired to maintain a given degree of coke loading, the regeneration step may be controlled such that the regenerated catalyst returning to the toluene methylation reaction zone is coke-loaded at the desired level.

The present process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

The process of the present invention is generally conducted at a temperature between about 500 and about 700° C., preferably between about 500 and about 600° C., a pressure of between about 1 atmosphere and 1000 psig (100 and 7000 kPa), a weight hourly space velocity of between about 0.5 and 1000, and a molar ratio of toluene to methanol (in the reactor charge) of at least about 0.2, e.g., from about 0.2 to about 20. The process is preferably conducted in the presence of added hydrogen and/or added water such that the molar ratio of hydrogen and/or water to toluene +methanol in the feed is between about 0.01 and about 10.

Figure 2:
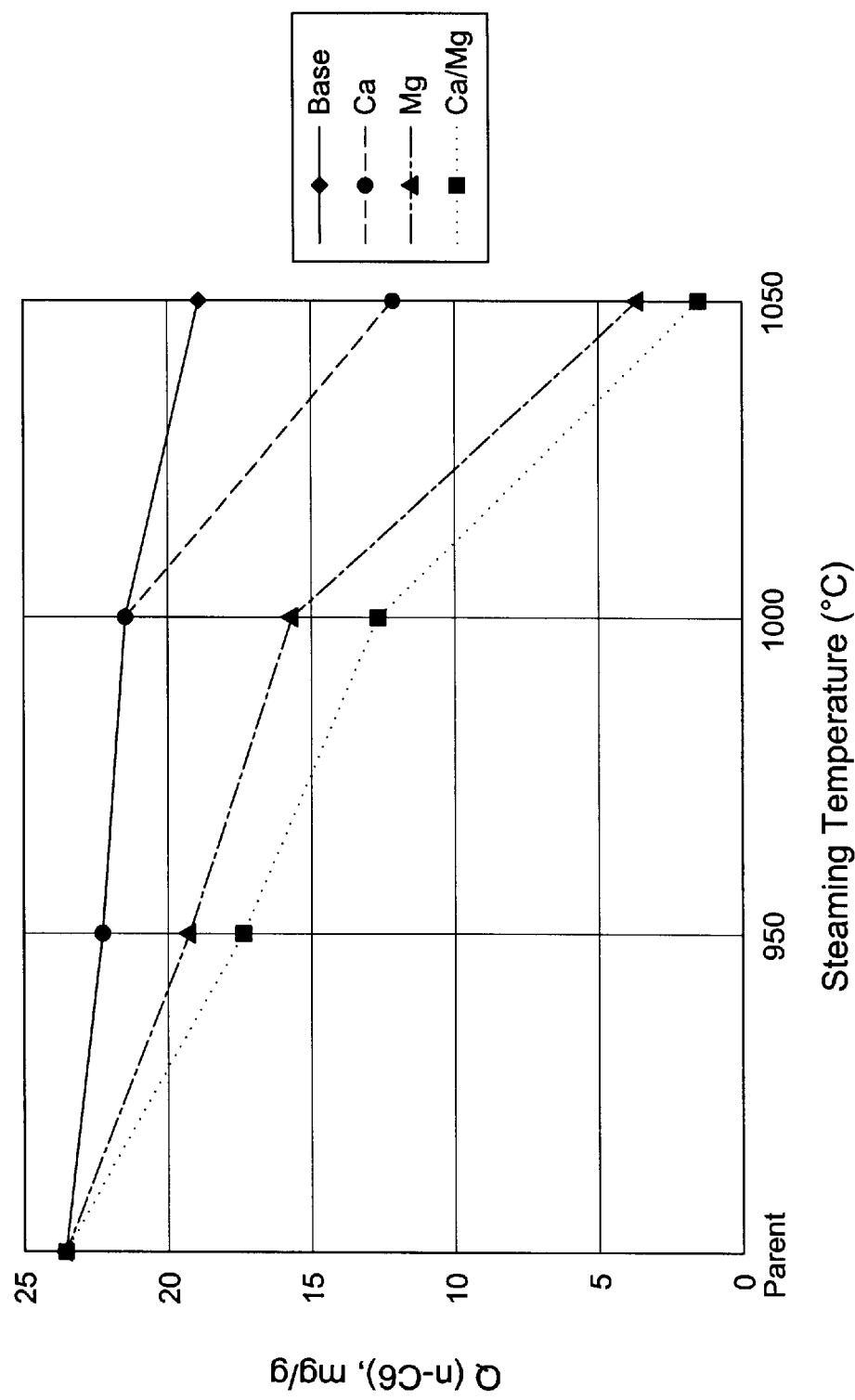
Figure 3:
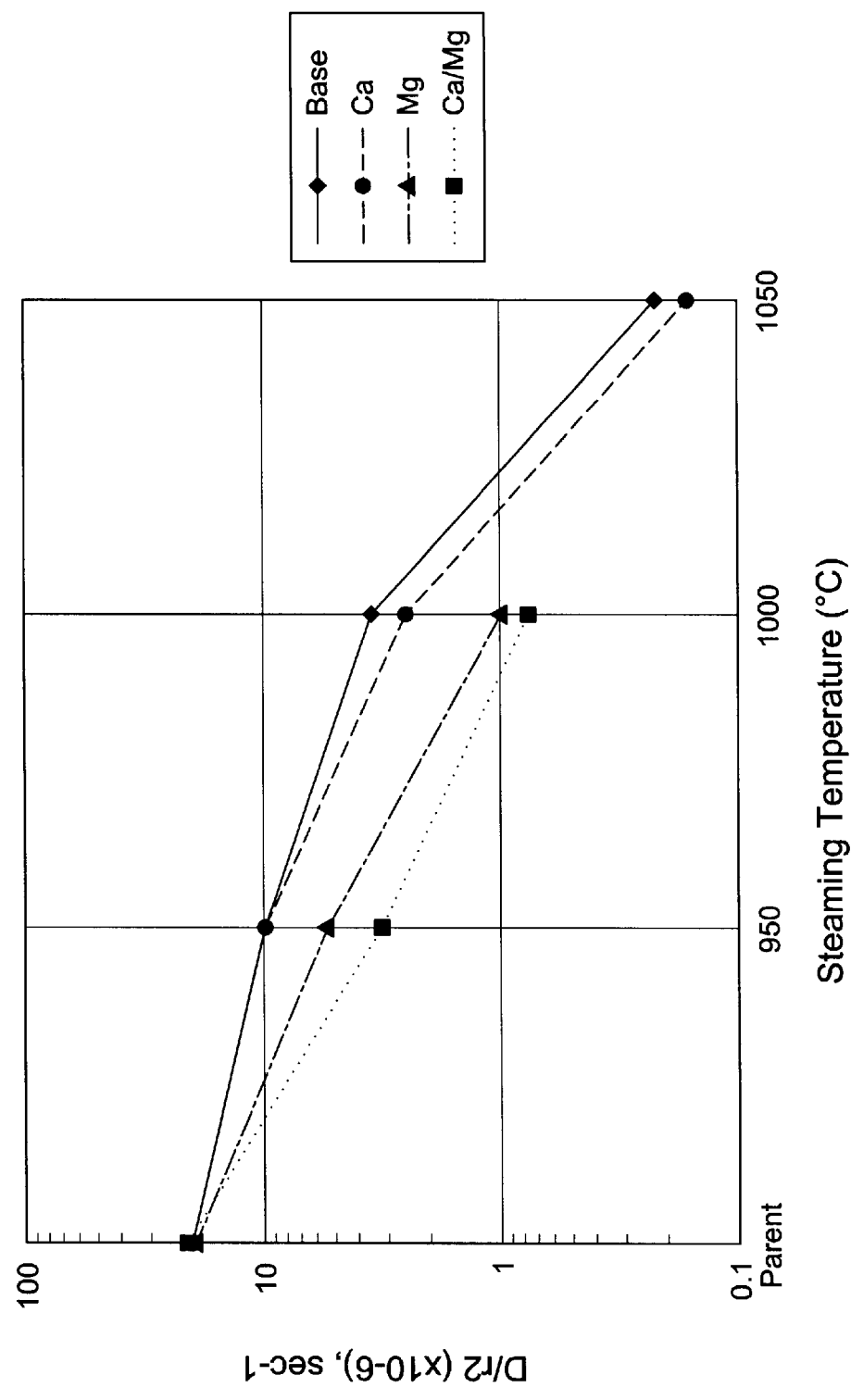

Using the process of the invention, toluene can be alkylated with methanol so as to produce para-xylene at a selectivity of at least about 90 wt % (based on total $C_8$ aromatic product) at a per-pass toluene conversion of at least about 15 wt % and a trimethylbenzene production level less than 1 wt %, The invention will now be more particularly described in the following Examples and the accompanying drawing, in which:

FIG. 1 is a graph of Diffusion Parameter against para-xylene yield and para-xylene selectivity for the catalyst of Examples 10–14; and FIGS. 2 and 3 are graphs of steaming temperature against n-hexane sorption capacity and Diffusion Parameter respectively for the catalysts of Example 15.

In the Examples, micropore volume (n-hexane) measurements were made on a computer controlled (Vista/Fortran) duPont 951 Thermalgravimetric analyzer. Isotherms were measured at 90° C. and adsorption values taken at 75 torr n-hexane. The diffusion measurements were made on a TA Instruments 2950 Thermalgravimetric Analyzer equipped with a Thermal Analysis 2000 controller, a gas switching accessory and an automatic sample changer. Diffusion measurements were made at 120° C. and 60 torr 2.2-dimethylbutane. Data were plotted as uptake versus square root of time. Fixed bed catalytic testing was conducted using a ⅜" (1 cm) outside diameter, down-flow reactor using a two gram catalyst sample. The product distribution was analyzed with an on-line Varian 3700 GC (Supelcowax 10 capillary column, 30 m in length, 0.32 mm internal diameter, and 0.5 μm film thickness).

Examples 1–5

Five samples of a composite catalyst containing 2.9 wt. % phosphorus and 10 wt % of a 450:1 $SiO_2/Al_2O_3$ ZSM-5 in a binder comprising silica-alumina and clay were steamed for 0.75 hours, one atmosphere steam at 975° C. (Example 1), 1000° C. (Example 2), 1025° C. (Example 3), 1050° C. (Example 4) and 1075° C. (Example 5). The effect of steaming temperature on the n-hexane sorption capacity (Q) compared to that of the unsteamed catalyst (10.7 mg/g) and on the Diffusion Parameter ($D/r^2 \times 10^6$) is summarized in Table 1 below.

Samples of the five steamed catalysts were then used in toluene methylation tests on a feed comprising toluene, methanol and water such that toluene/MeOH molar ratio=2 and $H_2O$/HC molar ratio=2 (where HC=toluene+methanol). The tests were conducted at 600° C., 40 psig (380 kPa) and HC WHSV=4 in the presence of hydrogen such that $H_2$/HC molar ratio=2 The results of Examples 2–5 are summarised in Table 2.

TABLE 1

| Catalyst ID | Steaming Temp (° C.) | Q (n-$C_6$, mg/g) | % retention of initial sorption capacity | $D/r^2$ sec$^{-1}$ (×10$^6$) |
| --- | --- | --- | --- | --- |
| Ex. 1 | 975 | 10.3 | 96 | 21.2 |
| Ex. 2 | 1000 | 9.7 | 91 | 16.4 |
| Ex. 3 | 1025 | 9.1 | 85 | 10.2 |
| Ex. 4 | 1050 | 8.4 | 79 | 3.2 |
| Ex. 5 | 1075 | 6.5 | 61 | 0.3 |

TABLE 2

| | Example 2 | Example 3 | Example 4 | Example 5 |
| --- | --- | --- | --- | --- |
| Temp, ° C. | 600.0 | 600.0 | 600.0 | 600.0 |
| Pressure, psig | 40.5 | 42.8 | 40.3 | 43.2 |
| WHSV | 4.0 | 4.0 | 4.0 | 4.0 |
| Time on Stream, hr | 4.8 | 20.6 | 5.1 | 5.0 |
| Product Distribution (wt %) | | | | |
| C5- | 1.42 | 0.73 | 0.99 | 1.44 |
| MeOH | 0.02 | 0.17 | 0.21 | 1.85 |
| BENZENE | 0.25 | 0.13 | 0.20 | 0.27 |
| TOLUENE | 61.82 | 62.41 | 66.27 | 81.63 |
| EB | 0.06 | 0.06 | 0.06 | 0.04 |
| P-XYL | 30.38 | 32.21 | 30.52 | 14.26 |
| M-XYL | 3.17 | 2.00 | 0.68 | 0.13 |
| O-XYL | 1.37 | 0.94 | 0.33 | 0.11 |
| ETOL | 0.30 | 0.33 | 0.31 | 0.14 |
| TMBENZENE | 1.05 | 0.92 | 0.37 | 0.08 |
| C10+ | 0.15 | 0.10 | 0.04 | 0.04 |
| | 100.00 | 100.00 | 100.00 | 100.00 |
| Performance Data | | | | |
| Toluene Conv. % | 33.21 | 32.56 | 28.39 | 11.80 |
| MeOH Conv. % | 99.71 | 97.76 | 97.76 | 75.12 |
| MeOH Utilization, mol % | 62.08 | 63.72 | 57.53 | 34.26 |
| p-Xylene Selectivity, % | 86.99 | 91.64 | 96.80 | 98.35 |
| Xylene Yield on Toluene, wt % | 37.73 | 37.98 | 34.07 | 15.67 |
| p-Xylene Yield on Tol, wt % | 32.8 | 34.8 | 33.0 | 15.4 |
| Xylenes/Aromatic Product, wt % | 95.1 | 95.8 | 97.0 | 96.2 |

From Table 2 it will be seen, with the catalyst of Examples 1–5, steaming at a temperature in excess of 1000° C. was necessary to reduce the $D/r^2$ value below 15 and with the Example 2 catalyst (steamed at 1000° C. to a $D/r^2$ value of 16.4), the p-selectivity of the catalyst was below 87%. As the steaming temperature increased above 1000 C. to 1075° C, the para-xylene selectivity increased but with the catalyst steamed at 1075° C. this was accompanied by a significant decrease in the paraxylene yield and the methanol utilization (moles of xylene produced/moles of methanol converted).

EXAMPLES 6–9

A second composite catalyst containing 4.5 wt % phosphorus and 10 wt. % of a 450:1 $SiO_2/Al_2O_3$ ZSM-5 in a binder comprising silica-alumina and clay was divided into four samples which were steamed for 0.75 hours, one atmosphere steam at 950° C. (Example 6), 975° C. (Example 7), 1000° C. (Example 8), and 1025° C. (Example 9). The effect of steaming temperature on the n-hexane sorption capacity (Q) and Diffusion Parameter ($D/r^2 \times 10^6$) of these catalysts is summarized in Table 3 below.

Samples of the four steamed catalysts were then used in toluene methylation tests conducted as in Examples 2–5 with the HC WHSV=4. The results of Examples 6–9 are summarised in Table 4.

TABLE 3

| Catalyst ID | Steaming Temp (° C.) | Q (n-C$_6$, mg/g) | % retention of initial sorption capacity | D/r2 sec$^{-1}$ (×10$^6$) |
| --- | --- | --- | --- | --- |
| Unsteamed Sample | | 12.7 | | 21.7 |
| Ex. 6 | 950 | 9.4 | 74 | 6.3 |
| Ex. 7 | 975 | 7.2 | 57 | 5.3 |
| Ex. 8 | 1000 | 7.9 | 62 | 1.92 |
| Ex. 9 | 1025 | 7.0 | 55 | 0.84 |

TABLE 4

| | Example 6 | Example 7 | Example 8 | Example 9 |
| --- | --- | --- | --- | --- |
| Temp, ° C. | 600.0 | 600.0 | 600 | 600 |
| Pressure, psig | 44.3 | 43.1 | 45.3 | 42.0 |
| WHSV | 4.0 | 4.0 | 4.0 | 4.0 |
| Time on Stream, hr | 6.3 | 5.9 | 5.9 | 5.9 |
| Product distribution, wt % | | | | |
| C5– | 1.70 | 1.68 | 1.69 | 1.57 |
| MeOH | 1.16 | 0.35 | 1.15 | 2.43 |
| BENZENE | 0.24 | 0.20 | 0.24 | 0.22 |
| TOLUENE | 65.17 | 67.30 | 73.76 | 83.83 |
| EB | 0.06 | 0.05 | 0.05 | 0.03 |
| P-XYL | 29.99 | 28.55 | 22.09 | 11.50 |
| M-XYL | 1.16 | 0.72 | 0.34 | 0.13 |
| O-XYL | 0.52 | 0.35 | 0.21 | 0.11 |
| ETOL | 0.31 | 0.28 | 0.21 | 0.11 |
| TMBENZENE | 0.63 | 0.46 | 0.27 | 0.07 |
| C10+ | 0.06 | 0.05 | 0.00 | 0.00 |
| | 100.00 | 100.00 | 100.00 | 98.43 |
| Performance Data | | | | |
| Toluene Conv. % | 29.73 | 27.44 | 20.47 | 9.62 |
| MeOH Conv. % | 97.81 | 95.17 | 84.14 | 66.42 |
| MeOH Utilization, mol % | 59.02 | 59.02 | 49.02 | 32.20 |
| p-Xylene Selectivity, % | 94.70 | 96.38 | 97.58 | 97.95 |
| Xylene Yield on Tol, wt % | 34.14 | 31.93 | 24.40 | 12.66 |
| p-Xylene Yield on Tol, wt % | 32.3 | 30.8 | 23.8 | 12.4 |
| Xylenes/Aromatic Product, wt % | 96.1 | 96.6 | 96.7 | 96.5 |

Comparative Example A

ZSM-5 crystals were prepared according to the method set forth in Example 33 of the Butter et al U.S. Pat. No. 3,965,209. The ZSM-5 had a silica to alumina molar ratio of about 70 to 1 and was combined with an alumina binder in a ratio of 65 weight % zeolite and 35 weight % binder.

The bound, phosphorus-free catalyst had an n-hexane sorption capacity, Q, of 74.4 mg/g and a Diffusion Parameter for 2,2-dimethylbutane of 740 sec$^{-1}$. The catalyst was steamed at 950° C. for 65 hours at atmospheric pressure (100 kPa) in 100% steam which reduced its n-hexane sorption capacity, Q, to 32.4 mg/g, or 44% of the initial capacity, and its Diffusion Parameter for 2,2-dimethylbutane to 1.72 sec$^{-1}$. The steamed catalyst was then subjected to catalytic testing in the same manner as Examples 1–9. In particular, experiments were conducted at 600° C., 40 psig (380 kPa), H$_2$/HC=2, H$_2$O/HC=2, WHSV=4 with a toluene/MeOH=2 feed. The results are summarized in Table 5, which provides data for an average analysis of three samples taken at 28.53. 33.32 and 37.22 hours on stream.

TABLE 5

| Temp, ° C. | 600 |
| --- | --- |
| Pressure, psig | 39.63 |
| WHSV | 4.00 |
| Time on Stream, hr | 33.0 |
| Product Distribution, wt % | |
| C5– | 0.36 |
| DME | 0.09 |
| MeOH | 1.35 |
| BENZENE | 0.19 |
| TOLUENE | 71.91 |
| EB | 0.05 |
| P-XYL | 21.40 |
| M-XYL | 1.91 |
| O-XYL | 1.18 |
| ETOL | 0.17 |
| TMBENZENE | 1.29 |
| C10+ | 0.09 |
| | 100.00 |
| Performance Data | |
| Toluene Conv. % | 22.30 |
| MeOH Conv. % | 80.74 |
| MeOH Utilization, mol % | 53.79 |
| p-Xylene Selectivity, % | 87.37 |
| Xylene Yield on Toluene, wt % | 26.47 |
| p-Xylene Yield on Toluene, wt % | 23.1 |
| Xylenes/Aromatic Product, wt % | 93.2 |

The data in Table 5 show that in Comparative Example A, although the toluene conversion was 22.30%, the para-selectivity was only 87.37%, the methanol conversion was only 80.74% and the wt % xylenes based on the total aromatic product was only 93.2. Furthermore, the yield of the unwanted byproduct, trimethylbenzene, was 1.29 wt. %.

EXAMPLES 10–14

A series of fluid bed catalysts were produced containing about 4 wt % phosphorus and 25 wt. % of a 450:1 SiO$_2$/Al$_2$O$_3$ ZSM-5 in a binder comprising kaolin clay. The catalysts were steamed for 0.75 hours at varying temperatures between 1025 and 1060° C. and were used to effect the alkylation of toluene with methanol in a bench-scale fluid bed reactor in the absence of cofed hydrogen. Details of the test and the results obtained are summarized in Table 6 and FIG. 1. It will be seen that, as the Diffusion Parameter of the catalyst decreased with increasing steaming severity, the para-xylene selectivity increased generally linearly whereas the para-xylene yield increased to a maximum at a D/r$^2$ value of 1–2×10$^{-6}$ sec$^{-1}$ before decreasing again.

TABLE 6

| Example No. | 10 | 11 | 12 | 13 | 14 |
| --- | --- | --- | --- | --- | --- |
| Catalyst Properties | | | | | |
| Phosphorus, wt % | 3.9 | 3.8 | 4.1 | 4.1 | 3.8 |
| Steaming Temp, C. | 1025 | 1031 | 1033 | 1033 | 1060 |
| D/r$^2$, sec-1 (×10$^6$) | 1.14 | 0.71 | 2.81 | 6.5 | 0.45 |
| Q, (n-C6) mg/g | 19.7 | 19 | 14.1 | 14.2 | 17.8 |
| Parent Q, mg/g | 21.6 | 21.6 | 17.1 | 20.7 | 21.9 |
| Reaction Conditions | | | | | |
| Feed Toluene/Methanol (mol/mol) | 2.08 | 2.03 | 1.93 | 2.06 | 2.17 |
| Feed H2O/HC (mol/mol) | 0.47 | 0.46 | 0.63 | 0.63 | 0.51 |
| Reactor Temp, F. | 1105 | 1107 | 1113 | 1108 | 1110 |
| Reactor P, psig | 20.6 | 20.7 | 20.8 | 21.7 | 20.7 |

TABLE 6-continued

| Example No. | 10 | 11 | 12 | 13 | 14 |
|---|---|---|---|---|---|
| HC WHSV | 1.71 | 1.75 | 1.75 | 1.72 | 1.71 |
| Time On Stream, Hrs | 10 | 10 | 10 | 10 | 2 |
| Feed Composition, wt % | | | | | |
| MeOH | 12.81 | 13.12 | 13.20 | 12.50 | 12.26 |
| Toluene | 76.76 | 76.53 | 73.19 | 73.93 | 76.51 |
| H2O | 10.43 | 10.35 | 13.61 | 13.57 | 11.23 |
| Product Composition, wt % | | | | | |
| C5− | 1.46 | 1.65 | 1.67 | 1.52 | 2.41 |
| MeOH | 0.01 | 0.03 | 0.09 | 0.01 | 0.29 |
| Benzene | 0.40 | 0.31 | 0.33 | 0.34 | 0.32 |
| Toluene | 54.60 | 55.89 | 50.81 | 52.41 | 62.16 |
| EB | 0.05 | 0.05 | 0.05 | 0.05 | 0.04 |
| p-Xylene | 22.15 | 21.68 | 21.72 | 19.85 | 15.70 |
| m-Xylene | 1.87 | 1.16 | 2.33 | 2.94 | 0.42 |
| o-Xylene | 0.78 | 0.50 | 1.00 | 1.25 | 0.20 |
| Styrene | 0.02 | 0.02 | 0.02 | 0.02 | 0.02 |
| E-Toluene | 0.25 | 0.25 | 0.23 | 0.23 | 0.20 |
| TMBenzene | 0.52 | 0.48 | 0.70 | 0.72 | 0.24 |
| C10+ | 0.28 | 0.34 | 0.31 | 0.30 | 0.39 |
| H2O | 17.61 | 17.64 | 20.74 | 20.36 | 17.61 |
| Performance Data | | | | | |
| Toluene Conv. % | 28.9 | 27.0 | 30.6 | 29.1 | 18.8 |
| MeOH Conv. % | 99.9 | 99.8 | 99.3 | 99.9 | 97.6 |
| MeOH Utilization, mol % | 58.5 | 53.8 | 57.7 | 58.1 | 41.1 |
| p-Xylene Selectivity, % | 89.3 | 92.9 | 86.7 | 82.6 | 96.2 |
| Xylene Yield on Tol, wt % | 32.3 | 30.5 | 34.2 | 32.5 | 21.3 |
| p-Xylene Yield on Tol, wt % | 28.9 | 28.3 | 29.7 | 26.8 | 20.5 |
| Xylenes/Aromatic Products, wt % | 95.7 | 95.3 | 95.0 | 94.8 | 94.8 |

EXAMPLE 15

A series of three catalysts similar to those of Examples 10–14 (25 wt % ZSM-5 of 450:1 silica/alumina ratio, 75 wt % clay binder with additional 4 wt % phosphorus) was prepared by doping respectively with calcium (2000 ppmw added), magnesium (5000 ppmw added), and both calcium and magnesium (2000 ppmw Ca/5000 ppmw Mg added). Slurries were prepared by mixing together components in the following order: ZSM-5 slurry, phosphoric acid, calcium/magnesium (from nitrate salts), and clay. Catalysts were spray dried and then air calcined at 540° C. for 3 hours. Three samples of each catalyst were then steamed for 45 minutes in 1 atmosphere steam at 950° C., 1000° C., and 1050° C., respectively. The n-hexane sorption capacity and the Diffusion Parameter of the catalysts are plotted against steaming temperature in FIGS. 2 and 3. The presence of magnesium (and calcium to a lesser extent) decreases the steaming temperature required to produce a catalyst with a given Diffusion Parameter. These data show that combinations of oxide modifiers can effectively be used to produce the desired catalyst.

EXAMPLE 16

A comparison was made between a catalyst similar to those used in Examples 10–14, in which the initial zeolite had a silica/alumina molar ratio of 450, and a catalyst produced from ZSM-5 having an initial silica/alumina molar ratio of 26. In each case the catalyst contained about 4 wt % phosphorus and 25 wt. % of ZSM-5 in a binder comprising kaolin clay and was steamed for 45 minutes at >1000° C. before being used to effect the alkylation of toluene with methanol in a fixed bed microunit. The results are summarized in Table 7 from which it will be seen that the 26:1 material had significantly lower activity (as indicated by the lower WHSV necessary to achieve comparable toluene conversion), lower para-selectivity and lower methanol utilization than the 450:1 material.

TABLE 7

| Catalyst Properties | | |
|---|---|---|
| Percent ZSM-5 | 25 | 25 |
| Si:Al Ratio | 450 | 26 |
| Steaming Temperature, ° C. | 1051 | 1016 |
| Reaction Conditions | | |
| Temperature, ° C. | 600 | 585 |
| Pressure, psig | 40 | 40 |
| WHSV | 8.0 | 2.50 |
| Tol/MeOH (mol/mol) | 2.0 | 2.00 |
| H2/HC (mol/mol) | 2.0 | 2.00 |
| H2O/HC (mol/mol) | 2.0 | 2.00 |
| Time on Stream, hr | 14.30 | 6.00 |
| Product composition, wt % | | |
| C5− | 0.05 | 2.12 |
| DME | 0.00 | 0.00 |
| MeOH | 0.40 | 0.32 |
| BENZENE | 0.13 | 0.23 |
| TOLUENE | 64.42 | 65.83 |
| EB | 0.06 | 0.05 |
| P-XYLENE | 32.66 | 27.82 |
| M-XYLENE | 0.94 | 1.81 |
| O-XYLENE | 0.42 | 0.75 |
| ETHYL TOLUENE | 0.33 | 0.25 |
| TMBENZENE | 0.56 | 0.76 |
| C10+ | 0.04 | 0.06 |
| Performance Data | | |
| Toluene Conv., % | 30.68 | 29.16 |
| MeOH Conv., % | 94.30 | 95.43 |
| MeOH Utilization, mol % | 67.37 | 59.46 |
| p-Xylene Selectivity, % | 96.02 | 91.58 |
| Xylene Yield on Tol, wt % | 36.61 | 32.69 |
| p-Xylene Yield on Tol, wt % | 35.2 | 29.9 |
| Xylenes/Aromatic Products, wt % | 96.8 | 95.7 |

EXAMPLES 17 and 18

Two composite catalysts were produced containing 10 wt % of 450:1 SiO$_2$/Al$_2$O$_3$ ZSM-5 in a kaolin clay matrix which in one case also contained 2.8 wt % phosphorus (Example 17) and the other case did not contain phosphorus (Example 18). Each catalyst was steamed at 1010° C. for 0.75 hour and was then used to effect the alkylation of toluene with methanol in a bench-scale fluid bed reactor containing 80 grams of catalyst. The properties of the steamed catalysts and the results of the toluene alkylation tests are shown in Table 8 below.

From Table 8 it will be seen that the Diffusion Parameter, $D/r^2$ of the phosphorus-free catalyst of Example 18 remained high after steaming. In addition, it will be seen that the para-xylene selectivity and yield of the phosphorus containing catalyst of Example 17 were significantly higher than those of the phosphorus-free catalyst of Example 18.

TABLE 8

| Example | 17 | 18 |
|---|---|---|
| Catalyst Properties | | |
| Phosphorus, wt % | 2.8 | 0 |

TABLE 8-continued

| Example | 17 | 18 |
|---|---|---|
| $D/r^2$, sec$^{-1}$ (×10$^6$) | 2.54 | 36.28 |
| Q, (n-C6) mg/g | 8.1 | 8.8 |
| Parent Q, mg/g | 8.4 | 10.6 |
| Feed Composition, wt % | | |
| MeOH | 12.82 | 13.15 |
| Toluene | 75.61 | 75.61 |
| H2O | 11.57 | 11.24 |
| TOTAL | 100 | 100 |
| Reaction Conditions | | |
| Feed Toluene/Methanol (mol/mol) | 2.05 | 2.00 |
| Feed H2O/HC (mol/mol) | 0.53 | 0.51 |
| Reactor Temp, F. | 1107 | 1108 |
| Reactor Pressure, psig | 19 | 21.6 |
| HC WHSV | 1.72 | 1.74 |
| Time On Stream, Hrs | 6 | 6 |
| Product Composition, wt % | | |
| C5– | 1.66 | 1.53 |
| MeOH | 0.34 | 0.33 |
| Benzene | 0.26 | 0.31 |
| Toluene | 55.09 | 54.33 |
| EB | 0.04 | 0.03 |
| p-Xylene | 20.08 | 15.94 |
| m-Xylene | 1.57 | 4.83 |
| o-Xylene | 0.72 | 2.3 |
| Styrene | 0.02 | 0.01 |
| E-Toluene | 0.23 | 0.17 |
| TMBenzene | 0.61 | 1.49 |
| C10+ | 0.29 | 0.25 |
| H2O | 19.09 | 18.48 |
| TOTAL | 100 | 100 |
| Performance Data | | |
| Toluene Conv. % | 27.1 | 28.1 |
| MeOH Conv. % | 97.3 | 97.5 |
| MeOH Utilization, mol % | 54.1 | 54.3 |
| p-Xylene Selectivity, % | 89.8 | 69.1 |
| Xylene Yield on Tol, wt % | 29.6 | 30.5 |
| p-Xylene Yield on Tol, wt % | 26.6 | 21.1 |
| Xylenes/Aromatic Products, wt % | 94.9 | 92.2 |

EXAMPLES 19–21

A base catalyst particle was prepared by spray-drying a mixture of ZSM-5 having a silica-alumina molar ratio of 450:1, kaolin clay and silica. After rotary calcination at 650° C. (1200° F.), the final composition of the catalyst was 40 wt % ZSM-5, 30 wt % kaolin and 30 wt % silica. The calcined catalyst was divided into three samples, which were impregnated by the incipient wetness techniques with solutions containing boron (Example 19), magnesium (Example 20) and lanthanum (Example 21) respectively and having the following compositions:

a) boron-containing solution
   20 gm boric acid
   800 gm distilled water
   8 gm 30 wt % ammonium hydroxide
b) magnesium-containing solution
   20 gm magnesium nitrate hexahydrate
   240 gm distilled water
c) lanthanum-containing solution
   20 gm lanthanum nitrate hexahydrate
   80 gm distilled water.

In each case, impregnation was conducted by incipient wetness by adding 0.79 gm of the appropriate solution to a catalyst sample, after which the sample was dried at 150°C. for 2 hours and then air calcined at 550° C. for 4 hours to convert the ammonium and nitrate salts to oxides. The oxide-modified catalysts were then heated in 1 atmosphere steam at 1000° C. Table 9 lists the oxide loading on each catalyst on an elemental basis and the n-hexane adsorption capacity (Q in mg/g) and Diffusion Parameter ($D/r^2 \times 10^6$ sec$^{-1}$) of the unsteamed and steamed catalysts.

TABLE 9

| | Oxide Loading | Q (n-C$_6$, mg/g) | $D/r^2$ sec$^{-1}$ (×10$^6$) |
|---|---|---|---|
| Unsteamed Catalyst | | | |
| Example 19 | 0.2 wt % boron | 52.6 | 17 |
| Example 20 | 0.5 wt % magnesium | 42.7 | 24.2 |
| Example 21 | 4.9 wt % lanthanum | 39.8 | 19.9 |
| Steamed Catalyst | | | |
| Example 19 | 0.2 wt % boron | 32.7 | 2.6 |
| Example 20 | 0.5 wt % magnesium | 37.3 | 9.4 |
| Example 21 | 4.9 wt % lanthanum | 31.1 | 1.4 |

The steamed catalysts of Examples 19 and 21 were then tested in the alkylation of toluene with methanol under the conditions and with the results listed in Table 10.

TABLE 10

| Example | 19 | 21 |
|---|---|---|
| Reaction Conditions | | |
| Temperature, C. | 592 | 592 |
| Pressure, psia | 16 | 16 |
| WHSV | 3 | 4 |
| Time on stream, minutes | 402 | 6 |
| Product Composition, wt % | | |
| C5– | 2.33 | 2.47 |
| Methanol | 0.59 | 3.18 |
| Benzene | 0.07 | 0.04 |
| Toluene | 64.6 | 67.54 |
| Ethylbenzene | 0.06 | 0.06 |
| P-xylene | 28.05 | 23.02 |
| M-xylene | 1.81 | 1.47 |
| O-xylene | 0.75 | 0.61 |
| Ethyltoluene | 0.31 | 0.30 |
| Trimethylbenzene | 1.08 | 0.78 |
| C10+ | 0.34 | 0.52 |
| Performance Data | | |
| % of total xylenes | | |
| Para | 91.6 | 91.71 |
| Meta | 5.90 | 5.85 |
| Ortho | 2.46 | 2.44 |
| Total xylenes, wt % | 30.61 | 25.10 |
| Xylenes/total aromatic product | 94.46 | 93.81 |
| Toluene conversion | 30.2 | 25.9 |
| Methanol conversion | 96.3 | 79.9 |
| Methanol utilization | 60 | 60 |

What is claimed is:
1. A method for producing a catalyst for use in the selective production of para-xylene by reacting toluene with methanol, said method comprising the steps of:
   (a) starting with a porous crystalline material having a Diffusion Parameter for 2,2-dimethylbutane in excess of 15 sec$^{-1}$ when measured at a temperature of 120° C. and a 2,2-dimethylbutane pressure of 60 torr (8 kPa); and (b) contacting the material of step (a) with steam at a temperature in excess of 1000° C. to reduce the Diffusion Parameter thereof for 2,2-dimethylbutane to about 0.1–15 sec$^{-1}$ when measured at a temperature of 120° C. and a 2,2-dimethylbutane pressure of 60 torr (8 kPa), the micropore volume of the steamed material being at least 50% of the unsteamed material.

2. The method of claim 1, wherein the porous crystalline material is combined with a source of at least one oxide modifier selected from the group consisting of oxides of elements of Groups IIA, IIIA, IIIB, IVA, VA, VB and VIA of the Periodic Table prior to step (b).

3. The method of claim 1, wherein the porous crystalline material is combined with a source of at least one oxide modifier selected from the group consisting of oxides of boron, magnesium, calcium, lanthanum and phosphorus prior to step (b).

4. The method of claim 1, wherein the porous crystalline material used in step (a) is an aluminosilicate zeolite having a Constraint Index of about 1 to 12.

5. The method of claim 4, wherein the zeolite has a silica to alumina molar ratio of at least 250.

6. The method of claim 1, wherein step (b) is conducted for about 10 minutes to about 100 hours.

7. The method of claim 2, wherein the catalyst contains about 0.05 to about 20 wt % of the oxide modifier based on the elemental modifier.

8. The method of claim 2, wherein the catalyst contains about 0.1 to about 10 wt % of the oxide modifier based on the elemental modifier.

9. The method of claim 5, wherein said zeolite is ZSM-5 or ZSM-11.

10. A process for the selective production of para-xylene which comprises reacting toluene with methanol under alkylation conditions in the presence of a catalyst produced by the method of claim 1.

* * * * *